(12) United States Patent
Neeff et al.

(10) Patent No.: US 7,919,632 B2
(45) Date of Patent: Apr. 5, 2011

(54) METHOD FOR PRODUCING CARBOXAMIDES

(75) Inventors: Arnd Neeff, Ennepetal (DE); Sergiy Pazenok, Solingen (DE)

(73) Assignee: Bayer Cropscience AG, Monheim (DE)

( * ) Notice: Subject to any disclaimer, the term of this patent is extended or adjusted under 35 U.S.C. 154(b) by 492 days.

(21) Appl. No.: 11/917,835

(22) PCT Filed: Jun. 7, 2006

(86) PCT No.: PCT/EP2006/005435
§ 371 (c)(1), (2), (4) Date: Jun. 11, 2008

(87) PCT Pub. No.: WO2006/136287
PCT Pub. Date: Dec. 28, 2006

(65) Prior Publication Data
US 2009/0054660 A1 Feb. 26, 2009

(30) Foreign Application Priority Data
Jun. 18, 2005 (DE) .......................... 10 2005 028 293

(51) Int. Cl.
*C07D 231/16* (2006.01)

(52) U.S. Cl. .................................................. 548/374.1
(58) Field of Classification Search ........................ None
See application file for complete search history.

(56) References Cited

U.S. PATENT DOCUMENTS
5,675,016 A * 10/1997 Gallenkamp et al. ...... 548/374.1
2009/0054661 A1 * 2/2009 Neeff et al. ................ 548/374.1

FOREIGN PATENT DOCUMENTS
| EP | 0 776 889 | 6/1997 |
| WO | 2006/092291 | 9/2006 |
| WO | WO 2006/092291 | 9/2006 |

OTHER PUBLICATIONS
International Search Report No. PCT/EP2006/005435, dated Oct. 6, 2006, 4 pgs.

* cited by examiner

*Primary Examiner* — Kamal A Saeed
(74) *Attorney, Agent, or Firm* — Baker Donelson Bearman, Caldwell & Berkowitz, PC

(57) ABSTRACT

The present invention relates to a novel process for preparing known fungicidally active 1,3-dimethyl-5-fluoro-1H-pyrazole-4-carboxamides from the corresponding acid fluoride and aniline derivatives in the absence of an acid acceptor.

7 Claims, No Drawings

METHOD FOR PRODUCING CARBOXAMIDES

CROSS-REFERENCE TO RELATED APPLICATIONS

The present application is a 371 of application Serial No. PCT/EP2006/005435, filed Jun. 7, 2006, which claims priority to German application no. DE 10 2005 028 293.8, filed Jun. 18, 2005.

BACKGROUND OF INVENTION

1. Field of Invention

The present invention relates to a novel process for preparing known fungicidally active 1,3-dimethyl-5-fluoro-1H-pyrazole-4-carboxamides from the corresponding acid fluoride and aniline derivatives in the absence of an acid acceptor.

2. Description of Related Art

It is already known that 1,3-dimethyl-5-fluoro-1H-pyrazole-4-carboxamides are obtained by reacting the corresponding acid fluoride with the desired aniline derivative (cf. EP-A 0 776 889). According to this description, preference is given to using bicyclic tertiary amines such as diazabicyclooctane (DABCO), diazabicyclononene (DBN) or diazabicycloundecene (DBU) as an acid acceptor. The reaction with DABCO affords only a yield of 80%. Moreover, DABCO is unsuitable for industrial scale implementations, since this reagent is very expensive and cannot be recycled.

SUMMARY OF INVENTION

It has now been found that carboxamides of the formula (I)

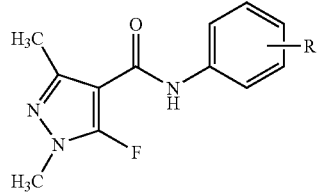

(I)

in which
R is $C_3$-$C_{12}$-cycloalkyl, $C_3$-$C_{22}$-cycloalkenyl, $C_6$-$C_{12}$-bicycloalkyl, $C_2$-$C_{12}$-oxacycloalkyl, $C_4$-$C_{12}$-oxacycloalkenyl, $C_3$-$C_{12}$-thiacycloalkyl, $C_4$-$C_{12}$-thiacycloalkenyl, $C_2$-$C_{12}$-azacycloalkyl, each of which may optionally be mono- or polysubstituted, identically or differently, by $C_1$-$C_8$-alkyl, $C_1$-$C_8$-alkoxy, halogen and/or cyano,
or phenyl which is optionally mono- to pentasubstituted identically or differently, where the substituents are each selected from the list $W^1$,
or unsubstituted $C_2$-$C_{20}$-alkyl,
or $C_1$-$C_{20}$-alkyl which is mono- or polysubstituted, identically or differently, by halogen, $C_1$-$C_6$-alkylthio, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulfinyl, $C_1$-$C_6$-haloalkylsulfonyl, $C_1$-$C_6$-haloalkoxy, $C_1$-$C_6$-haloalkylamino, halodi($C_1$-$C_6$-alkyl)amino, —$SiR^1R^2R^3$ and/or $C_3$-$C_6$-cycloalkyl, where the cycloalkyl moiety may in turn optionally be mono- to tetrasubstituted, identically or differently, by halogen, $C_1$-$C_4$-alkyl and/or $C_1$-$C_4$-haloalkyl, $W^1$ is halogen, cyano, nitro, amino, hydroxyl, $C_1$-$C_8$-alkyl, $C_1$-$C_8$-alkoxy, $C_1$-$C_8$-alkylthio, $C_1$-$C_8$-alkylsulfinyl, $C_1$-$C_8$-alkylsulfonyl, $C_2$-$C_6$-alkenyl, $C_2$-$C_6$-alkenyloxy; $C_1$-$C_6$-haloalkyl, $C_1$-$C_6$-haloalkoxy, $C_1$-$C_6$-haloalkylthio, $C_1$-$C_6$-haloalkylsulfinyl or $C_1$-$C_6$-haloalkylsulfonyl having in each case from 1 to 13 identical or different halogen atoms; $C_2$-$C_6$-haloalkenyl or $C_2$-$C_6$-haloalkenyloxy having in each case from 1 to 11 identical or different halogen atoms; $C_3$-$C_6$-cycloalkyl or $C_3$-$C_6$-cycloalkyloxy;
$R^1$ and $R^2$ are each independently hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl,
$R^3$ is hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or in each case optionally substituted phenyl or phenylalkyl,
characterized in that
5-fluoro-1,3-dimethyl-1H-pyrazole-4-carbonyl fluoride of the formula (II)

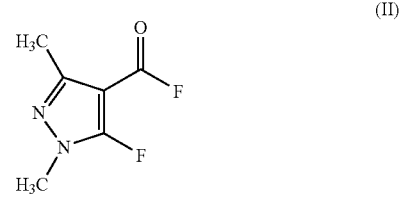

(II)

is reacted with aniline derivatives of the formula (III)

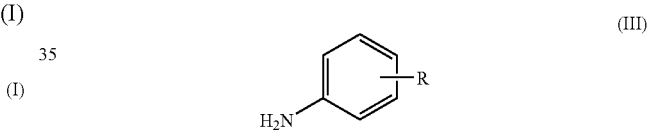

(III)

in which R is as defined above,
in the absence of an acid acceptor.

Surprisingly, the carboxamides of the formula (I) can be prepared under the inventive conditions with good yields in high purity and selectivity. A further advantage of the process according to the invention is that the workup is simpler, since the use of an acid acceptor is dispensed with. The process according to the invention also becomes more economically viable as a result. In addition, the reaction time can be shortened.

DETAILED DESCRIPTION OF PREFERRED A EMBODIMENT

When, for example, 5-fluoro-1,3-dimethyl-1H-pyrazole-4-carbonyl fluoride and 2-(1,3-dimethylbutyl)phenylamine are used as starting materials, the process according to the invention can be illustrated by the following formula scheme:

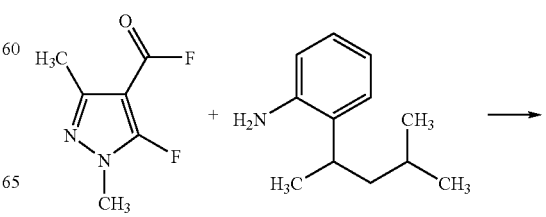

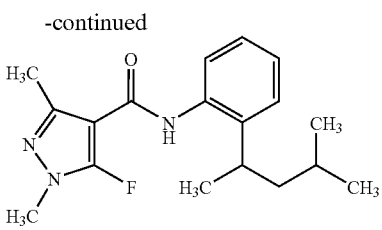

The 5-fluoro-1,3-dimethyl-1H-pyrazole-4-carbonyl fluoride of the formula (II) used as a starting material in the performance of the process according to the invention is known (cf. EP-A 0 776 889).

The aniline derivatives also used as starting materials in the performance of the process according to the invention are defined in general by the formula (III).

R is preferably $C_3$-$C_8$-cycloalkyl, $C_3$-$C_8$-cycloalkenyl, $C_6$-$C_{10}$-bicycloalkyl, $C_2$-$C_7$-oxacycloalkyl, $C_4$-$C_7$-oxacycloalkenyl, $C_3$-$C_7$-thiacycloalkyl, $C_4$-$C_7$-thiacycloalkenyl, $C_2$-$C_7$-azacycloalkyl, each of which may optionally be mono- to tetrasubstituted, identically or differently, by $C_1$-$C_4$-alkyl, $C_1$-$C_4$-alkoxy, fluorine, chlorine, bromine and/or cyano, or phenyl which is mono- to trisubstituted identically or differently, where the substituents are selected from the list $W^1$, or unsubstituted $C_2$-$C_{12}$-alkyl (such as ethyl and straight-chain or branched propyl, butyl, pentyl, hexyl, heptyl, octyl, nonyl, decyl, undecyl and dodecyl)

or $C_1$-$C_{12}$-alkyl (such as methyl, ethyl and straight-chain or branched propyl, butyl, pentyl, hexyl, heptyl, octyl, nonyl, decyl, undecyl and dodecyl) which is mono- or polysubstituted, identically or differently, by fluorine, chlorine, bromine, iodine, $C_1$-$C_6$-alkylthio, $C_1$-$C_4$-alkylsulfinyl, $C_1$-$C_4$-alkylsulfonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulfinyl, $C_1$-$C_4$-haloalkylsulfonyl, $C_1$-$C_4$-haloalkoxy, $C_1$-$C_4$-haloalkylamino, halodi($C_1$-$C_4$-alkyl)amino having in each case from 1 to 9 fluorine, chlorine and/or bromine atoms, —$SiR^1R^2R^3$, cyclopropyl, dichlorocyclopropyl, cyclobutyl, cyclopentyl or cyclohexyl.

R is more preferably cyclopentyl, cyclohexyl, cycloheptyl, bicyclo[2.2.1]heptyl, or mono-4-substituted phenyl, phenyl disubstituted identically or differently in the 3,4-, 2,3-, 2,4- or 3,5-position, or phenyl trisubstituted identically or differently in the 2,4,6-position, where the substituents are each selected from the list $W^1$, or unsubstituted $C_3$-$C_{10}$-alkyl (such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl) or $C_1$-$C_{10}$-alkyl (such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-di-methylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-di-methylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl) which is mono- or polysubstituted identically or differently by fluorine, chlorine, methylthio, ethylthio, n- or isopropylthio, n-, iso-, sec-, tert-butylthio, pentylthio, hexylthio, methylsulfonyl, ethylsulfonyl, n- or isopropylsulfonyl, n-, iso-, sec-, tert-butylsulfonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylthio, trifluoromethoxy, —$SiR^1R^2R^3$, cyclopropyl, dichlorocyclopropyl, cyclobutyl, cyclopentyl or cyclohexyl.

$W^1$ is preferably fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy.

$W^1$ is more preferably fluorine, chlorine or bromine.

$R^1$ and $R^2$ are each independently preferably $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^1$ and $R^2$ are each independently more preferably methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^1$ and $R^2$ are each independently most preferably methyl, methoxy, methoxymethyl or methylthiomethyl.

$R^1$ and $R^2$ are especially preferably each methyl.

$R^3$ is preferably $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^3$ is more preferably methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^3$ is most preferably methyl, ethyl, n- or isopropyl, iso- or tert-butyl, methoxy, isopropoxy, iso- or tert-butoxy.

$R^3$ is especially preferably methyl.

Preference is given to using aniline derivatives of the formula (III-1)

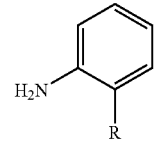

(III-1)

in which R is as defined above,
in the process according to the invention.

Preference is also given to using aniline derivatives of the formula (III-2)

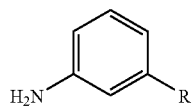

in which R is as defined above,
in the process according to the invention.

Preference is also given to using aniline derivatives of the formula (III-3)

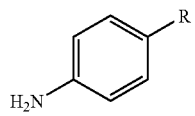

in which R is as defined above,
in the process according to the invention.

Particular preference is given to using aniline derivatives of the formula (III-1).

Aniline derivatives of the formula (III) or (III-1), (III-2) and (III-3) are known or can be prepared in a known manner (cf. EP-A 0 776 889, WO 03/010149).

The process according to the invention can be performed in the presence of a diluent. Useful diluents for this purpose include all inert organic solvents, preferably aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, more preferably chlorobenzene or toluene.

The reaction temperatures in the performance of the process according to the invention can be varied within a relatively wide range. In general, temperatures of from 120° C. to 150° C., preferably temperatures of from 130° C. to 140° C., are employed.

In the performance of the process according to the invention, generally between 0.8 and 1.5 mol, preferably equimolar amounts, of aniline derivatives of the formula (III) are used per mole of the 5-fluoro-1,3-dimethyl-1H-pyrazole-4-carbonyl fluoride of the formula (II).

Depending on the reactivity of the reactants, the reaction time may be up to 10 hours, but the reaction can also be terminated even earlier in the case of complete conversion. Preference is given to reaction times of 5 hours.

All processes according to the invention are generally performed under standard pressure. However, it is possible to work under elevated or reduced pressure—generally between 0.1 bar and 10 bar.

The carboxamides of the formula (I) preparable by the process according to the invention are value fungicides (cf., for example, WO 03/010149).

The inventive preparation of carboxamides of the formula (I) is described in the examples which follow, which further illustrate the above description. However, the examples should not be interpreted in a restrictive manner.

PREPARATION EXAMPLES

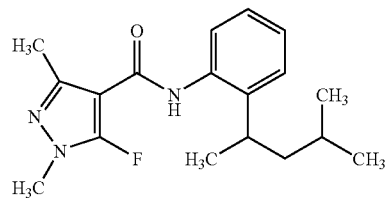

Under protective gas (argon), a solution of 2-(1,3-dimethylbutyl)phenylamine 18.05 g (100 mmol) in 40 ml of chlorobenzene is initially charged. 16.17 g (100 mmol) of 5-fluoro-1,3-dimethyl-1H-pyrazole-4-carbonyl fluoride are added and the mixture is stirred at 130° C. for a further 5 h. For workup, the mixture is allowed to cool, 100 ml of water are added and the mixture is extracted three times with 100 ml each time of ethyl acetate. The combined organic phases are washed once with 100 ml of water, dried over magnesium sulfate and concentrated under reduced pressure. The resulting suspension is stirred at room temperature with 100 ml for a further 2 h. This gives 28.2 g (89% of theory) of N-[2-(1,3-dimethylbutyl)phenyl]-5-fluoro-1,3-dimethyl-1H-pyrazole-4-carboxamide in the form of crystals (melting point 104-106° C.).

The invention claimed is:
1. A process for preparing a carboxamide of formula (I)

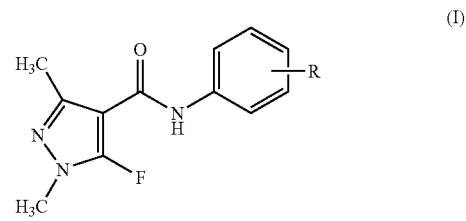

in which
R is $C_3$-$C_{12}$-cycloalkyl, $C_3$-$C_{12}$-cycloalkenyl, $C_6$-$C_{12}$-bicycloalkyl, $C_2$-$C_{12}$-oxacycloalkyl, $C_4$-$C_{12}$-oxacycloalkenyl, $C_3$-$C_{12}$-thiacycloalkyl, $C_4$-$C_{12}$-thiacycloalkenyl, $C_2$-$C_{12}$-azacycloalkyl, each of which may optionally be mono- or polysubstituted, identically or differently, by $C_1$-$C_8$-alkyl, $C_1$-$C_8$-alkoxy, halogen and/or cyano, or phenyl which is optionally mono- to pentasubstituted identically or differently, where the substituents are each selected from the list $W^1$,
or unsubstituted $C_2$-$C_{20}$-alkyl,
or $C_1$-$C_{20}$-alkyl which is mono- or polysubstituted, identically or differently, by halogen, $C_1$-$C_6$-alkylthio, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulfinyl, $C_1$-$C_6$-haloalkylsulfonyl, $C_1$-$C_6$-haloalkoxy, $C_1$-$C_6$-haloalkylamino, halodi($C_1$-$C_6$-alkyl)amino, —$SiR^1R^2R^3$ and/or $C_3$-$C_6$-cycloalkyl, where the cycloalkyl moiety may in turn optionally be mono- to tetrasubstituted, identically or differently, by halogen, $C_1$-$C_4$-alkyl and/or $C_1$-$C_4$-haloalkyl, $W^1$ is halogen, cyano, nitro, amino, hydroxyl, $C_1$-$C_8$-alkyl, $C_1$-$C_8$-alkoxy, $C_1$-$C_8$-alkylthio, $C_1$-$C_8$-alkylsulfinyl, $C_1$-$C_8$-alkylsulfonyl, $C_2$-$C_6$-alkenyl, $C_2$-$C_6$-alkenyloxy; $C_1$-$C_6$-haloalkyl, $C_1$-$C_6$-haloalkoxy, $C_1$-$C_6$-haloalkylthio, $C_1$-$C_6$-haloalkylsulfinyl or $C_1$-$C_6$-haloalkylsulfonyl having in each case from 1 to 13 identical or different halogen atoms; $C_2$-$C_6$-haloalkenyl or $C_2$-$C_6$-haloalkenyloxy having in each case from 1 to 11 identical or different halogen atoms; $C_3$-$C_6$-cycloalkyl or $C_3$-$C_6$-cycloalkyloxy;

$R^1$ and $R^2$ are each independently hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, $R^3$ is hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or in each case optionally substituted phenyl or phenylalkyl, said process comprising:

reacting 5-fluoro-1,3-dimethyl-1H-pyrazole-4-carbonyl fluoride of formula (II)

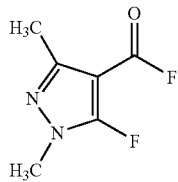

(II)

with aniline derivatives of formula (III)

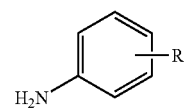

(III)

in which R is as defined above,
in the absence of an acid acceptor.

2. The process as claimed in claim 1, wherein a temperature of from 120° C. to 150° C. is employed.

3. The process as claimed in claim 1, wherein an aniline derivative of formula (III-1)

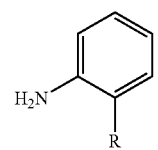

(III-1)

is used.

4. The process as claimed in claim 1 wherein 2-(1,3-dimethylbutyl)phenylamine is used as the aniline derivative of the formula (III).

5. The process as claimed in claim 2, wherein a temperature of from 120° C. to 150° C. is employed.

6. The process as claimed in claim 2, wherein 2-(1,3-dimethylbutyl)phenylamine is used as the aniline derivative of the formula (III).

7. The process as claimed in claim 3, wherein 2-(1,3-dimethylbutyl)phenylamine is used as the aniline derivative of the formula (III).

* * * * *